Figure 1:
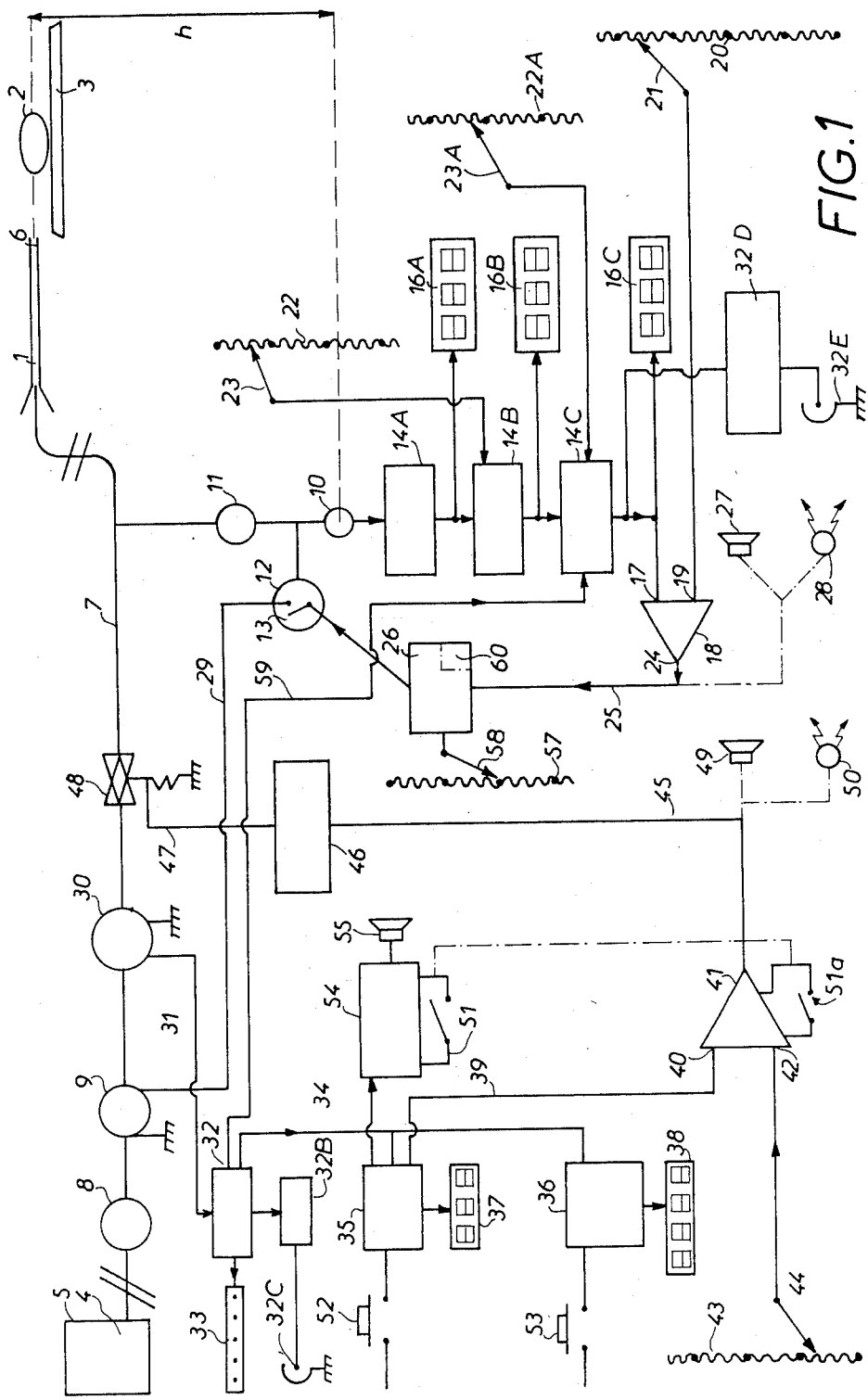

United States Patent [19]
Burner

[11] Patent Number: 4,795,424
[45] Date of Patent: Jan. 3, 1989

[54] APPARATUS FOR CONTROLLED IRRIGATION OF THE NATURAL CAVITIES AND TUBES OF THE HUMAN BODY

[76] Inventor: Robert Burner, 6, rue de la Sinne, 68100, Mulhouse, France

[21] Appl. No.: 142,319

[22] Filed: Dec. 30, 1987

Related U.S. Application Data

[63] Continuation of Ser. No. 865,205, filed as PCT FR85/00233 on Aug. 29, 1985, published as WO86/01390 on Mar. 13, 1986, abandoned.

[30] Foreign Application Priority Data

Aug. 31, 1984 [FR] France .................................. 84 13550
Aug. 31, 1984 [FR] France .................................. 84 13551

[51] Int. Cl.⁴ ............................................. A61M 1/03
[52] U.S. Cl. ............................................ 604/30; 128/4
[58] Field of Search ............... 128/DIG. 12, DIG. 13, 128/4, 5, 6, 7; 417/38, 412, 476, 477; 604/30, 31, 43, 67

[56] References Cited

U.S. PATENT DOCUMENTS 3,900,022 8/1975 Widran ........................... 128/303.15
4,529,397 7/1985 Hennemuth et al. ............. 604/30 X
4,551,131 11/1985 Miles ..................................... 604/31
4,589,280 5/1986 Carlin .............................. 604/67 X

FOREIGN PATENT DOCUMENTS 2039083 10/1979 United Kingdom .................. 604/31

Primary Examiner—Edward M. Coven
Attorney, Agent, or Firm—Frost & Jacobs

[57] ABSTRACT

The invention concerns an apparatus for controlled irrigation of the natural cavities and tubes of the human body. It is characterized in that it includes correcting means for equalizing the measuring signal which represents the pressure and which is emitted by a pressure gauge (10) according to the pressure losses and according to the difference of height between the area of measurement of the pressure and the intervention area which corresponds to an organ (2). These correcting means include a correcting circuit (14B) adapted to effect a correction according to said difference of height and a correcting circuit (14C) adapted to take into account the pressure loss, namely the flow rate of the fluid injected through the inner duct (6) of the endoscope (1) and the cross section of this duct.

19 Claims, 2 Drawing Sheets

APPARATUS FOR CONTROLLED IRRIGATION OF THE NATURAL CAVITIES AND TUBES OF THE HUMAN BODY

This is a continuation of application Ser. No. 06/865295, filed as PCT FR85/00233 on Aug. 29, 1985, published abandoned.

The present invention relates to an apparatus for controlled irrigation of the natural cavities and tubes of the human body, namely for endoscope, in particular for urological endoscope which include at least one duct to inject, either intermittently or continuously, an irrigation fluid in a corporeal cavity and conduit intervention area, so as to permit interventions as well with intermittent as with continuous irrigation, this apparatus comprising:

a tank which contains the irrigation fluid;

a Joining conduit for connecting this tank to the duct;

a supply pump which is mounted on the joining conduit for supplying the duct with irrigation fluid;

first means sensitive to pressure, which are connected below the pump to the joining conduit, for measuring the instant pressure being in this conduit at the level of these means sensitive to the pressure and for emitting a measuring signal representing this pressure;

and means for defining an acceptable maximum pressure in said intervention area.

It is known that in endoscopy certain procedures, be they only examinational or even surgical, require the presence of a generally aqueous fluid in the intervention area. The same applies, in particular, to urological endoscopy, namely for the bladder, ureters, urethra, prostate or kidneys. However, more generally, this requirement is also present in the case of natural or pathological cavities, which must be examined or treated by resection for example, or a simple lavage . or irrigation.

When performing endoscopy in an artificial fluid environment, either a continuous or an intermittent irrigation, with or without a liquid flow, is applied.

In the first case, the fluid is injected through a duct of the endoscope and withdrawn either through another duct of this endoscope, or by other means, such as a catheter. In the second case, one and the same duct of the endoscope serves to inject and withdraw the fluid.

Both in the continuous and intermittent irrigation, the injection is nowadays accomplished by gravity with the use of a tank with fluid, which is at a higher level than the endoscope in its working position. With this arrangement, the pressure of the fluid injected into the intervention area is, in principle, determined by the height of the fluid column between the endoscope and the fluid level in the tank.

In the case of intermittent irrigation, the withdrawal of the fluid is nowadays performed through the manual activation of the physician who, either opens an outlet stopcock or similar valve which is mounted on the sheath of the endoscope, or extracts the set of working elements with telescope from the sheath of the endoscope. This method presents no major drawbacks because the area of examination or operation has simply to be emptied.

In the case of continuous irrigation, the withdrawal of the fluid is nowadays performed either through the outlet duct when a two-way endoscope is used, or through a catheter when a one-way endoscope is used. In both cases the withdrawal is obtained either by means of the gravity of the fluid which must be withdrawn, or by a pump with selected but constant flow rate.

A first problem arises when, due to the fluid consumption, the level of the fluid to be injected from the tank changes with time. This calls either for an adaptation to the developing change in pressure, or for placing the tank at an accordingly higher level.

A second problem arises, in the case of continuous irrigation, inasmuch as it is not always easy to satisfactorily regulate the withdrawal of the fluid. A too great withdrawal lowers the pressure in the intervention area, whereas a too small withdrawal bears the risk that a dangerous overpressure develops in this area.

The pressure value in the intervention area is in a direct relationship with the fullness of this area, i.e., with the volume of the fluid it contains. An incomplete filling may adversely affect the quality of the examination and Jeopardize the surgical phase, whereas an excessive fullness i.e., a too high pressure may endanger the patient, in particular, in the case of surgery. Otherwise, if the flow rate of the withdrawal is or becomes superior to the flow rate of the injection the fullness of the intervention area is incomplete, which engenders the first above mentioned drawback. On the contrary, if the flow rate of the withdrawal is becomes inferior to the flow rate of the injection, the fullness of the intervention area s excessive, which causes an excessive pressure in the intervention area and generates the second above mentioned drawback.

As a result, the physician has to carefully see that the pressure of the fluid is neither too high nor too low by means of a simultaneous supervision of the injection and the withdrawal of the irrigation fluid. These supervisions impose on him task which is added to the always delicate duties, as are involved in the order endoscopic procedure. In addition, with the conventional systems of irrigation, the physician has only a very limited, even uncertain knowledge of the instant flow rate, of the volume of the injected fluid and of the volume of the withdrawn fluid, which practically hinders all accurate supervision of these different: parameters.

The object of the present invention is to eliminate all these disadvantages by the apparatus of the present invention for controlled irrigation, which allows to one work under a constant and lowest possible pressure in the case of continuous irrigation, and which allows to one work at an increasing but limited pressure which is situated under a threshold that cannot be overstepped, in the case of :

This object is reached by the apparatus according to the invention, which includes correcting means for equalizing a measuring signal which represents the pressure according, on the one hand to the pressure losses, and on the other to the difference of level, which exists between the above mentioned means sensitive to the pressure and the intervention area, so as to determine the value of the instant pressure at the level of the intervention area, and means for controlling the injection of the irrigation fluid, so that the pressure in the intervention area is at each instant inferior or equal to the acceptable maximum pressure.

According to another object of the invention, the means for equalizing the signal in accordance with pressure losses comprises a correcting circuit which is coupled with a controllable correcting circuit provided with a control organ designed to deliver to the correcting circuit distinct signals, which correspond respectively to different hydraulically equivalent cross sections of the inner duct of the endoscope, these different hydraulically equivalent cross sections being selected by means of the control organ.

In a preferred embodiment, the means for equalizing the signal according to pressure losses include a signal processing unit which is designed to receive an order signal representing the different hydraulically equivalent cross sections of the inner duct of the endoscope, this order signal being transmitted by a selecting circuit provided with a regulating organ, this signal processing unit being also designed to receive a flow rate signal transmitted by a unit which is activated by the fluid propelled by the pump, and to furnish to the correcting circuit a correcting signal, this correcting signal being in accord with the injection flow rate measured and regulated according to the order signal of the flow rate.

In this same preferred embodiment of the apparatus according to the invention, the means for equalizing the signal according to the pressure losses includes a circuit, which regulates and preselects the flow rate of the injection, and which comprises a regulating organ. This circuit and this regulating organ are designed to deliver distinct signals to a control unit of the supply pump, these distinct signals corresponding to different values of the flow rate of the fluid injected into t intervention area, these different values being displayed by means of the regulation organ.

Still in this preferred embodiment, these means for equalizing the signal according to the difference of level include a correcting circuit which is coupled with a controllable correcting circuit that comprises a regulating organ. This controllable correcting circuit and this regulating organ are designed to deliver to the correcting circuit distinct signals which respectively correspond to distinct differences of level between the means sensitive to pressure and the intervention area, these distinct differences of level being displayed by means of the regulating organ.

In the preferred embodiment of the apparatus according to the invention, the means for defining an acceptable maximum pressure in the intervention area include a control circuit equipped with a regulating organ. This circuit and this regulating organ are designed to deliver to a first input of a comparator distinct signals which respectively correspond to different values of the acceptable maximum pressure in the intervention area, these different values being displayed by means of said regulating organ.

In a particularly advantageous embodiment, the apparatus includes different devices of visual display which are respectively designed to visualize the instant pressure in the intervention area, the instant pressure measured by the first means sensitive to pressure, and the instant pressure in the inner duct of the endoscope.

The apparatus according to the invention otherwise includes preferably a unit designed to emit a signal representing the flow rate of the injected fluid and a processing unit which is connected with at least one volume counter of the fluid delivered by the pump and with the correcting circuit.

In a preferred embodiment, the apparatus includes two counters
of which the first is designed to measure the volume of the delivered fluid since the beginning of a current cycle, in the case of an intermittent irrigation, and of which the second is designed to measure the volume of the delivered fluid since the beginning of the procedure, whatever the manner of irrigation is In a particularly advantageous embodiment, the apparatus includes a preselection circuit which comprises a regulating organ that is designed to emit signals to a comparator, these signals corresponding to different volumes of fluid to be delivered during a procedure or a current cycle, these different volumes being selected by means of the regulating organ.

In this case, the comparator can include a first input for signals which proceed from the preselection circuit and correspond to different volumes of fluid, and a second input for signals which are emitted by the first counter.

Each of the first and second counter is preferably associated with respectively a first and a second visual display.

For permitting the injection of the fluid in the intervention area to be stopped when a predetermined volume of this fluid has been injected, the apparatus, according to a preferred embodiment, includes a first and a second zero-resetting device, these devices being respectively associated with the first counter and with the second counter, the first zero-resetting device being designed to act on a comparator which is coupled with a command unit of an electric valve that is interposed on the conduit.

In order to connect the injection device of the irrigation apparatus according to the invention with an active and controlled withdrawing device, it includes two adaptation circuits which are designed to amplify and adjust respectively the signals representing the flow rate and the instant pressure in the intervention area, as well as two terminal connections for connecting the two adaptation circuits.

In a particularly interesting embodiment, in the apparatus for irrigation according to the invention, the active and controlled withdrawal device includes a conduit for fluid from the intervention area, a withdrawal pump which is mounted on this conduit, and second means sensitive to the pressure connected on the conduit below the intervention area, correcting means for equalizing the measuring signal emitted by the second means sensitive to pressure according on the one hand to the pressure losses, and on the other hand to the difference of level, which exists between the second means sensitive to the pressure and the intervention area, and means for controlling the withdrawal of the irrigation fluid so that the pressure in the intervention area is at all times inferior or equal to the acceptable maximum pressure.

In this case, the correcting means for equalizing the measuring signal emitted by the second means sensitive to pressure according to the pressure losses, includes preferably a comparison and processing unit and a correcting circuit equipped with a regulating organ. This circuit and this organ are designed to deliver to the unit different signals which respectively correspond to different hydraulically equivalent cross sections of the outlet conduits, these different hydraulically equivalent cross sections being selected by means of the regulating organ.

In this case as well, the means for equalizing the signal according to the pressure losses includes preferably a correcting circuit equipped with a preselection organ, this correcting circuit and this preselection organ being designed for selecting the predetermined flow rates of the fluid withdrawn from the intervention are. They likewise include a terminal connection which is connected with a correcting circuit equipped with a regulating organ arranged for taking into account a signal representative of the instant flow rate of the injection device.

In this case at least, the means for equalizing the signal according to the difference of level includes preferably a controllable correcting circuit equipped with a preselection organ, this circuit and this organ being arranged for delivering to a correcting circuit distinct signals which respectively correspond to distinct differences of the level between said second means sensitive to the pressure and the intervention area, these distinct differences of the level being selected by means of the preselection organ.

Figure 2:
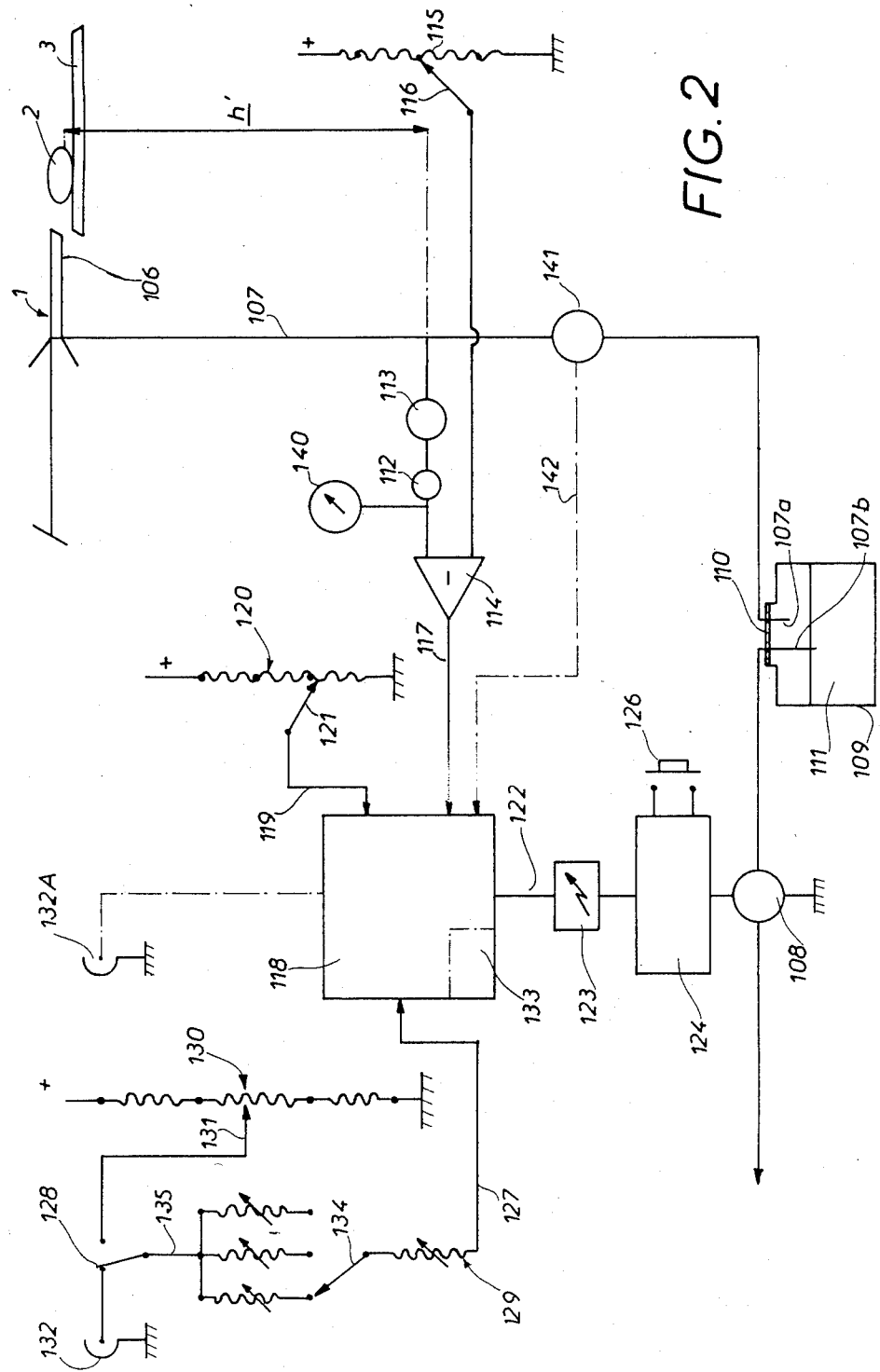

The present invention will be better understood in reference to the description of examples of realization and to the attached drawing in which:

The FIG. 1 represents a schematic view of a preferred embodiment of the injection device of the irrigation apparatus according to the invention, and The FIG. 2 represents a schematic view of a preferred embodiment of the withdrawing device of the irrigation apparatus according to the invention.

In reference to FIG. 1, the represented device comprises an endoscope 1, which serves to examine and/or surgically treat an organ 2 having a cavity so as e.g. the bladder of a patient lying on a table 3. As previously indicated, for this kind of intervention it is necessary to fill the cavity of the bladder with a irrigation fluid 4, initially contained in a tank 5, which is introduced into the bladder through an inner duct 6 of the endoscope via a conduit 7 equipped with a filter 8.

During the intervention, the irrigation fluid 4 can be delivered to the endoscope and therefore injected into the organ 2 either continuously or intermittently.

This injection is obtained by means of a pump 9, e.g., like a magnet drive gear pump, which is mounted on the conduit 7 between the endoscope and the filter and which is designed for delivering in a controlled manner the fluid to the endoscope. Between the endoscope and the pump, there is accommodated on conduit 7 a pressure gauge 10, which preferably is hydraulically isolated from fluid 4 by a separating means 11, i.e. of the type having a diaphragm or the like, as well as safety pressure gauge 12 with a variable taring means, which disconnects a switch 13, when the maximum safety pressure is exceeded.

Pressure gauge 10 is provided for measuring the instant pressure present at its level in conduit 7 and for emitting an appropriate measuring signal, whereas pressure gauge 12 is arranged for connecting switch 13 as long as this instant pressure is below a predetermined maximum safety pressure.

The device otherwise includes a processing unit 14A designed to bring to a form the measuring signal emitted by pressure gauge 10. Its output signal is directed, on the one hand, to a first visual display 16A which is designed to indicate to the physician the instant pressure present at the level of pressure gauge 10, and, on the other, to a correcting circuit 14B which is designed to emit a correcting signal by means of a controllable correcting circuit 22 that includes a slide 23. With the use of this controllable correcting circuit, the physician can regulate the amplitude of the correcting signal emitted to the correcting circuit 14B, this amplitude representing the difference of level h between pressure gauge 10 and intervention area defined by organ 2 or more specifically, the extremity of endoscope 1. For example, it can be assumed that controllable correcting circuit is intended to furnish seven discrete correcting values which correspond to differences of level ranging from 0–30 cm.

The output signal of correcting circuit 14B is directed, on the one hand, to a second visual display 16B, designed or show the physician the instant pressure in conduit 7 at the level of the endoscope, and, on the other, to another correcting circuit 14C, which receives a correcting signal from another controllable correcting circuit 22A, for example of the type with slide 23A that is intended for permitting the physician to regulate the amplitude of the correcting signal emitted to circuit 14C, this amplitude representing the cross section of the inner duct 6 of the endoscope. For example, the controllable correcting circuit 22A is designed to permit delivery of three discrete correcting values, which correspond to hydraulically equivalent cross sections measuring 3, 5 and 7 $mm^2$. Correcting circuit 14C is otherwise designed to receive, via a line 59, a second correcting signal from a unit 32, which will be described further below, and which emits, on said line 59, a signal which corresponds to the flow rate of the injection.

As a result, in circuit 14C, the measuring signal of the pressure, already corrected according to the difference in level between the measuring point and the endoscope, is thus corrected according to the cross section of the passage of fluid 4 in the inner duct 6 of the endoscope, and according to the flow rate of the injection. In other terms, the measuring signal of pressure is corrected according to the pressure loss which results from these two factors.

The output signal of correcting circuit 14C is directed, on the one hand, to a visual display 16C designed to permit the physician to show the thus-equalized pressure, and, on the other, to an input 17 of a comparison circuit 18, the other input 19 of which receives a reference signal from a control circuit, schematically indicated at 20, which allows the physician to regulate, with slide 21, or the like, the tolerable maximum pressure in the intervention area defined by organ 2, during the procedure, and change therefore the characteristics of the signal directed to input 19. For example, twelve discrete values to regulate the tolerable maximum pressure in the intervention area may be foreseen, which range from 5–60 cm water column. Alternatively, one could also foresee a working of the comparison circuit 18 so that the flow rate is regulated in such manner that pressure in the intervention area does not exceed a predetermined value selected by the physician. To that effect, the physician selects said pressure by means of the control circuit 20, with help of slide 21.

Display 16C is most useful for the physician, since it allows him to monitor the actual pressure within the organ 2. Furthermore, the displays 16A and 16B represents very efficacious means of supervision for him, since they permit a permanent monitoring of the equalization which is connected with the difference of level h previously defined.

Due to the corrections which are connected, on one hand, with the difference of level h between the pressure gauge and the endoscope, on the other hand, with the cross section of the inlet of the endoscope, and at last, with the flow rate of the injection, the physician can, as needed, change the working height, exchange the endoscope and/or vary the rate of flow, without having to worry about a possible change of pressure in organ 2 which might not have been detected. These corrections likewise allow to recognize, with the aid of a pressure measurement outside of organ 2, the actual pressure in organ 2 with an adequate accuracy, without having to make any calculation and without having to modify the endoscope by equipping it with a pressure detector.

The comparison signal which appears o outlet 24 of comparator 18, is delivered, via a line 25, to a control unit 26 of the pump and, optionally, to audio signalling means 27 and/or visual signalling means 28. These signalling means are provided to emit a signal when the preselected maximum pressure is reached. Unit 26 control a supply unit 29 of pump 9, on which switch 213 is installed. If needed, additional correcting means 60 may be provided, which are connected with the temperature of the pressure-sensitive means, this temperature being dependent on the ambient temperature, namely on that of the fluid and that of the pressure gauge 12.

Control unit 26 is connected to a unit 57 which regulates and preselects the flow rate of the injection. This regulating circuit may include a slide 58, with the help of which the physician can regulate the amplitude of the control signal, this amplitude corresponding to a best adapted flow rate or a given intervention. Different values of regulating of the flow rate can be provided, these values ranging, for example, from $0-700$ cm$^3$.

In operation, as long as the pressure present in conduit 7 at the level of the endoscope and, by means of the above corrections, in organ 2, is below the maximum reference pressure which is indicated on control circuit 20, the pump is actuated and the fluid is supplied to the endoscope to be injected into said organ. As soon as the maximum reference pressure is reached, comparator 18 controls unit 26 which disconnects the pump and thus stops the supply of fluid to the endoscope. If, for any cause, the pressure in conduit 7 would reach the maximum safety value to which pressure gauge 12 is tared, switch 13 will disconnect and thus stop pump 9.

The described device advantageously includes furthermore additional means which are designed to measure the volume of the fluid which has been injected since the beginning of an intervention in progress. These additional means are particularly useful in the case of a procedure with an intermittent irrigation. In the described example, these means are controlled by an element 30 which is mounted in series on conduit 7 below pump 9. The element 30 is actuated by the fluid delivered by the pump, and emits a signal representative of the flow rate, for example, impulses, the frequency of which is proportional to the rate of flow,. element 30 may be composed in the form of a gear and may be integrated in pump 9. The impulses emitted by element 30, each of which represents a volume unit, are conducted, via a line 31, to a signal processing unit 32, which actuates a visual display 33, of the type having electro-luminescent diodes or the like, which shows the physician the instant rate of flow. Unit 32 also controls, via its outlet line 34, a first and a second counter 35, 36. Each of the counters 35 and 36 is respectively connected with a visual display 37 and 38 designed to permit the physician to show the volumes calculated by counting the impulses emitted by element 30 and made in visual form by unit 32.

The first counter 35 is directed to measure, in the case of an intermittent irrigation, the volume of the fluid released since the beginning of the current cycle. This same counter 35 controls an element 54 intended to deliver, by means of an acoustical device 55, acoustic signals, for example of the following kind:

(a) when a manually actuated switch 51 which controls element 54, is in the position "Limited Volume":

| | | |
|---|---|---|
| from 0 to 200 cm$^3$: one acoustic signal | /10 cm$^3$ | ⎫ deep |
| from 200 to 300 cm$^3$: two acoustic signals | /10 cm$^3$ | ⎬ |
| from 300 to 400 cm$^3$: three acoustic signals | /10 cm$^3$ | ⎭ tone |
| from 400 to 500 cm$^3$: one acoustic signal | /10 cm$^3$ | ⎫ high |
| from 500 to 600 cm$^3$: two acoustic signals | /10 cm$^3$ | ⎭ tone |

(b) when switch 51 is in the position: "No Limited Volume", one acoustic signal /10 cm$^3$ is produced.

Counter 36 is intended to measure, whatever the manner of irrigation is, i.e. continuous or intermittent, the volume of the fluid released since the beginning of the procedure.

The result of counter 35 is delivered, via a line 39, to an input 40 of a comparison circuit 41, the other input of which receives a reference signal which comes from a regulating circuit schematically indicated at 43. This regulating circuit allows the physician to regulate, with the aid of a slide 44 or the like, the volume of the fluid which is to be released during the procedure or the current cycle. For example, ten discrete values for regulating the volume to be injected may be assumed, which range from 150–600 cm$^3$.

The signal triggered by the comparison is delivered, via a line 45, to a unit 46, which controls the supply line 47 of an electric valve 48 mounted on conduit 7. As long as the volume measured by counter 35 is below the volume determined by preselection unit 43, the comparison signal will leave electric valve 48 open. However, in contrast thereto, as soon as the measured volume equals this preselected volume, unit 46 commands the closing of electric valve 48, and thus, the supply of fluid to the endoscope is discontinued. The comparison signal, transmitted via line 45, may control acoustic alarm means 49 or visual alarm means 50, which emit a signal as soon as the preselected maximum volume is reached.

In a preferred embodiment, control unit 26 and control unit 46 may be interconnected, so that pump and electric valve are simultaneously controlled.

Naturally, this comparison between supplied volume and reference volume is only significant for procedures involving intermittent irrigation. For this reason, a switch 51a is provided for procedures with continuous irrigation, which is coupled with a manual switch 51, which, in one of its two positions, corresponding to continuous irrigation, constantly actuates unit 46 Through comparator 41, so as to control electric valve 48, so that this valve remains open, and which, in the other position corresponding to intermittent irrigation, make comparator 41 control the unit 46.

Each of counters 35 and 36 is respectively provided with a zero resetting means and 53, which may be actuated automatically by connecting the device or manually by the physician. Fluid is injected as long as the volume released posteriorly to the preceding zero reset is less than the preselected maximum volume, for example 400 cm³. The moment that this volume reaches this value, 400 cm³ in this example, the injection is automatically stopped and can be only resumed following another zero reset by push button 52, after the intervention area has been emptied. Furthermore, the physician can stop the injection at any moment, before the volume reaches this value.

As a result of the foregoing, the above described apparatus permits a preselection of the maximum pressure in the intervention area, provides a visual and/or acoustical monitoring of the instant pressure in the intervention area and allows a regulation of this maximum pressure during the procedure, as well as an automatic actuation of the supply pump by the physician himself, without the assistance of another person.

Furthermore, in its preferred embodiment which includes the measuring means of the volume of the released fluid, the device allows
- a preselection of the volume to be released per cycle in the case of an intermittent irrigation,
- a permanent visual and/or acoustic monitoring of the released volume and flow rate,
- a regulation of the reference volume during the procedure,
- as well as an automatic interruption of the fluid flow, when the reference volume is reached.

In the alternative pump 9 could be continually actuated, and electric valve 48 could be set up in the form of a three-way valve with a return-flow to tank 5. Such a three-way valve would also be controlled by unit 26.

For the purpose of withdrawing the fluid from organ 2, all suitable means, whether inert or active, regulated or non-regulated, may be used in the case of continuous or of intermittent irrigation. However, an appreciable additional safety is obtained by utilization of an active and controlled withdrawing means, which will be described below with more detail. Therefore the above described device is equipped with adaptation circuits 32B and 32D which are unit 32 which represents a flow rate meter, and the information of the instant pressure in the intervention area which is coming from circuit 14C, these means being adapted to supply terminal connections 32C and 32E in order to take this information into consideration.

The drainage device of the irrigation apparatus, of which the injection device is above described, will be presented with more details in reference with FIG. 2.

In the represented example, the drainage device comprises a drainage conduit 107 which is connected with a second inner duct 106 of the endoscope 1. However, in certain cases, the drainage duct 107 could be connected with a catheter (not represented) which opens into the organ 2.

Otherwise, this device includes a pump 108, for example of the peristaltic type, which is mounted on the conduit 107. In practice, an intermediate tank 109 is interposed on conduit 107 above the pump 108, so that the two branches 107a and 107b, respectively the inlet and outlet branches of conduit 107, cross in air tight manner a plug 110 of this tank. The extremity of the inlet branch 107a is preferably placed above the level of the fluid 111, while the outlet branch 107b is placed in the superior zone of this fluid, which thus constitutes a reserve.

A pressure gauge 112, hydraulically isolated from irrigation fluid by a separating means 113, for example of the type having a diaphragm, is mounted on the conduit 107, abreast between the end 1 and the intermediate tank 109. This pressure gauge 112 is designed to measure the instant pressure which exists, at its level, in the drainage conduit 107.

Accordingly to a particularly advantageous embodiment of the device, the signal emitted by the pressure gauge 112 and which is representative of the pressure that exists in conduit 107 at the level of this gauge, is corrected so as to be faithfully representative of the pressure which exists within organ 2. Therefore, the device includes a correcting circuit 114, for example a subtractor, designed to subtract from the measuring signal delivered by pressure gauge 112 a correcting signal coming from a controllable correcting circuit 115, for example of the type with potentiometer, which allows the physician to regulate, with help of a slide 116 or the like, the amplitude of the correcting signal emitted to correcting circuit 114, this amplitude being representative of the h' of level between the endoscope 1 and the pressure gauge 112. For example, the correcting scale can comprise seven discrete values which correspond to differences of level ranging from 100–130 cm.

Just as in the case of the injection device described with reference to the FIG. 1, the physician can, according to need, change the working height without having to worry about a possible change of pressure caused within the organ 2 and which would be consequential to this modification of the working height. This property of the device also allows, by means of a pressure measurement outside of organ 2 and of an appropriate correcting, to recognize the actual pressure in organ 2 with an adequate accuracy, without having to make calculations and without having to modify the endoscope, for example by equipping it with a pressure detector. In other words, the physician can employ common endoscopes and benefit at the same time by real improvements and great precision in the work.

The output signal of correction circuit 114 is transmitted via a line 117 and directed to a comparison, correcting and processing unit 118. This unit also receives on an inlet line 119 a reference signal which proceeds from a control circuit 120, with the use of which the physician can, with help of a slide 121 or the like, control the intravesical pressure that is permissible in organ 2 during the intervention. For example, one can foresee a correcting such as the actual pressure in the intervention area corresponding to maximum values ranging from 5–60 cm water column.

The comparison signal, which appears after processong on an outlet line 122 of the comparison unit 118, controls optionally through an opto-electronic coupling organ 123, a control unit 124 of the pump 108. This control unit 124 of the pump can advantageously be equipped with a push button 126 for the control of the purge. A visual display 140, for example of the type with galvanometer, can be mounted on the output of the pressure gauge 112 or of the subtractor 114, so as to give the physician an indication of the measured actual pressure.

According to an advantageous characteristic of the device, the measuring signal of the instant pressure which appears on line 117 is corrected so as to take into account the cross sections of the drainage conduits, namely the hydraulically equivalent cross section of the duct 106, as well as the drainage flow rate, these two parameters engendering a depression which is added to the measuring signal of line 117.

The correcting signal appears on an additional inlet line 127 of comparison unit 118. The line 127 proceeds from a correcting circuit 129 which takes into account the cross sections of duct 106. The circuit 129 is equipped with a control organ 134, for example with slide, which moves between terminals that correspond respectively to diverse cross sections. The correcting circuit 129 is controlled by means of a which appears on its inlet 135 and which proceeds from a switch 128. This switch can occupy two positions, namely a first position in which it is connected, via a terminal connection 132, with the controlled injection device, described in reference to FIG. 1, and which delivers to this terminal a signal that represents said injection flow, rate (in the case such a device is used), and a second position in which, it is connected with a slide 131 of a correcting circuit 130 of which the terminal correspond to different injection flow rates which the physician selects according to the actual flow rate, in the case of an injection of fluid by simple gravity, the display of the flow rate being effected in this case by the display of the height of the tank which contains the irrigation fluid, the fluid level in this tank being kept constant, for example by means of the suspension of the tank by help of an adequate selected spring.

As indicated in the figure, the represented draining device can optionally include an additional correcting circuit 133 which takes into account the temperature of the means sensitive to pressure, the temperature being namely dependant on the ambient temperature, on that of the fluid, as well as on that of the pressure gauge.

Although the device can be used independently of the injection device, namely in combination with an injection system by gravity, this device finds its preferred utilization in the interventions with continuous irrigation in which pressure and irrigation flow rate are controlled and constant. In working, so long as the pressure, measured by the pressure gauge 112 and corrected by the circuits 115, 129, 133 and 130 or 120, is inferior to or equals the operation pressure displayed by the physician on circuit 120, the pump 108 is at a standstill. Contrarily, when this pressure is reached or overstepped, pump 108 is started.

In the case device is used with an inert injection device by gravity, it represents a regulator thanks to the permanent control of the pressure. In this case, comparison unit 118 can advantageously use the information of flow rate delivered by a means sensitive to the flow rate 141, which is mounted on conduit 107 above the intermediate tank 109. The information of flow rate delivered by said means 141, known in itself, on a line 142, as well as the information of pressure delivered by unit 114 on line 117, will permit comparison unit 118 to correct the flow rate of the withdrawal, so as the pressure in the intervention area keeps a constant value which is selected by means of slide 121 of the control circuit 120.

In case this controlled draining device is used with a controlled injection device, it offers to the latter an additional safety. In this case, the comparison unit 118 can advantageous - use the information of pressure in the intervention area which is delivered by the injection device on the terminal connection 132A, for regulating the flow rate of the withdrawal in order to keep this pressure at a constant value which is selected on the injection device.

At last, the device can also be used in the interventions with intermittent. irrigation when a one-way endoscope equipped with an outlet stop cock, i.e. equipped with two stop-cocks (for example a sheath with central valve) is used In this case, the control of withdrawal is executed by the comparison unit 118 which warrants the role of a safety organ.

While injections during endoscopic interventions in urology were until now obtained by gravity, thus bringing a whole approximate, even hazardous, knowledge and mastery of the hydraulic parameters, namely the volume, the flow rate and the pressure, the above described invention permits, by means of an electronically regulated injection, optionally completed by an active and controlled draining, to remove the above mentioned coercions and hazards thanks to a perfect and exact knowledge as well as an entire mastery of the hydraulic parameters, at every instant. The result is a safety for the patient thanks to the total elimination of the overpressures and its complications, as well as a considerable improvement of the operative conditions for the surgeon thanks to the gain of a maximum visibility in the intervention area and the instance of irrigation. In particular, the apparatus allows the improvement of the visibility in the intervention area, and therefore the increase of the operative comfort. The surgeon being discharged of the controlling and adjustment problems, can dedicate a more important part of his time to the operation itself and make his intervention surer and more efficient.

To sum up the injection with electronic regulation used in intermittent irrigation allows in a.11 endoscopic interventions:

1. The selection of the hydraulic parameters of the injection:
   maximum pressure of the fluid in the intervention area;
   instant flow rate of the injected fluid;
   maximum volume of the liquid to be injected per cycle.
2. The constant display, visual and/or acoustical, of the instant value of these parameters:
   instant pressure in the intervention area;
   instant flow rate of the injected fluid;
   volume of the fluid injected since the beginning of the cycle and since the beginning of the intervention.
3. The instantaneous foot control of the fluid injection and of the electric operation current.
4. The correction of the operating table height, i.e., equalization of the changes, as are determined by the physician, in height of the operating table, i.e., of the organ to be operated.

The electronically regulated injecting apparatus used with continuous irrigation allows the same results as these above mentioned. While in intermittent irrigation the proper intervention is realized only during the phase of the injection of the fluid, in continuous irrigation the operation is executed during all the duration of the irrigation, the draining being executed either through a special conduit of the endoscope, or through a vesical trocard.

The electronically regulated draining permits:
1. The selection of the pressure in the intervention area, namely the interventions under low pressure.
2. The automatic regulation of the hydraulic parameters of the suction:
   constant pressure in the interventin area;
   suction flow flow rate, for all values of this injection flow rate;
   constant vesical volume.

3. The constant display of the instant value of the suction.

4. The correction of the operating table height.

The present invention is not limited to the described forms of realization and illustrated by the figures, but can sustain different modifications and present diverse variants evident for those skilled in the art.

I claim:

1. Apparatus for controlled irrigation of the natural cavities and tubes of the human body by endoscopy, wherein an urological endoscope having at least one duct is provided to inject an irrigation fluid intermittently or continuously in a corporeal cavity and/or a corporeal intervention area whereby to permit interventions both with intermittent and continuous irrigations, said apparatus comprising:

an urological endoscope having at least one duct;
a tank containing irrigation fluid;
a joining conduit connecting said tank to said at least one duct;
a supply pump mounted on said joining conduit supply said duct with irrigation fluid;
first means sensitive to pressure, connected below said pump to said joining conduit, for measuring the instant pressure in said conduit at the level of said first means for emitting a measuring signal representing this pressure;
second means, communicating with said first means, for defining an acceptable maximum pressure in said intervention area;
correcting means receiving said measuring signal for equalizing said measuring signal which represents the pressure which is a resultant of pressure losses and of the difference in level existing between said first means and said intervention area, whereby to determine the value of said instant pressure at the level of said intervention area; and
means connecting said pump, said second means and said correcting means including a control unit in a supply conduit to said pump for controlling the injection of irrigation fluid in such manner that said pressure in said intervention area is at all times not greater than said acceptable maximum pressure.

2. Apparatus according to claim 1, wherein said correcting means for equalizing said measuring signal in accordance with said pressure losses comprises a correcting circuit coupled with a controllable correcting circuit having a control organ, said controllable correcting circuit and said control organ being connected and delivering to said correcting circuit distinct signals which correspond respectively to different hydraulically equivalent cross sections of the inner duct of said endoscope, said different hydraulically equivalent cross sections being selected by means of said control organ.

3. Apparatus according to claim 2, including means for measuring the volume of fluid injected, comprising an element actuated by fluid propelled by said pump and emitting a flow rate signal, a signal processing unit connected to said correcting circuit and adapted to receive an order signal representing said different hydraulically equivalent cross sections of said inner duct of said endoscope, said order signal being transmitted by a selecting unit provided with a regulating organ, said signal processing unit being also coupled to receive said flow rate signal transmitted by said element which is actuated by fluid propelled by said pump, and to actuate a visual display showing the instant rate of flow.

4. Apparatus according to claim 3, wherein said element actuated by the fluid propelled by said pump is connected in series in said joining conduit below said pump and is adapted for emitting a signal in the form of impulses which represents the flow rate of the injected fluid, and including at least one volume counter of the fluid volume delivered by said pump to said correcting circuit, said counter being connected to said signal processing unit.

5. Apparatus according to claim 4, including two said counters connected to said signal processing unit, the first of which is adapted for measuring the volume of fluid delivered since the beginning of a current cycle in the case of intermittent irrigation, and the second of which is adapted for measuring the volume of fluid delivered since the beginning of intervention by either mode of irrigation.

6. Apparatus according to claim 5, including a regulated circuit provided with a control organ adapted for emitting signals to a comparison circuit, said signals corresponding to different fluid volumes which are to be delivered during an intervention or a current cycle, said different volumes being selected by means of said control organ, said comparison circuit including a first input for said signals which proceeds from said regulated circuit and which corresponds to said different volumes of fluid, and a second input for signals which are emitted by said first counter.

7. Apparatus according to claim 5, wherein each of said first and second counters is connected respectively with a first and a second visual display device.

8. Apparatus according to claim 5, including a comparator, a first zero resetting device and a second zero resetting device, said resetting devices being connected respectively with said first counter and with said second counter, and wherein said first zero resetting device is adapted to act on said comparator which is coupled with a control unit of an electric valve interposed in said joining conduit, so as to stop the injection of fluid when a predetermined volume has been injected into said intervention area.

9. Apparatus according to claim 4, including two adaptation circuits designed to amplify and adapt respectively the signals representative of the flow rate and of the instant pressure in said intervention area, an active and controlled withdrawing device, and terminal connections for communicating said adaptation circuits with said active and controlled withdrawing device.

10. Apparatus according to claim 9, wherein said active and controlled withdrawing device includes a conduit for withdrawing the fluid of said intervention area, a withdrawing pump mounted on said conduit, second means sensitive to pressure connected to said conduit above said intervention area, said withdrawing device including correcting means for equalizing the measuring signal emitted by said first means representing said pressure, which exists between said first means and said intervention area, and means for controlling the withdrawing of the irrigation fluid, whereby said pressure in said intervention area is at any instant not greater than said maximum pressure.

11. Apparatus according to claim 10, wherein said correcting means for equalizing the measuring signal emitted by said first means includes a comparison and processing unit and a correcting circuit equipped with a control organ, said correcting circuit and said organ being adapted to emit to said comparison and processing unit different signals corresponding respectively to different hydraulically equivalent cross sections of said duct in said endoscope, said different hydraulically equivalent cross sections being preselected by means of said control organ.

12. Apparatus according to claim 10, wherein said correcting means for equalizing said measuring signal according to pressure losses includes a correcting circuit having a preselecting organ, said correcting circuit having terminals corresponding to different injection flow rates and said preselecting organ being adapted to preselect from said terminals the flow rates of fluid withdrawn from said intervention area.

13. Apparatus according to claim 10, wherein said correcting means for equalizing said measuring system according to said pressure losses includes a terminal connection connected with a correcting circuit which is in contact with a control organ, said terminal connection delivering to said correcting circuit a signal representative of the instant flow rate of said injection device.

14. Apparatus according to claim 10, wherein said correcting means for equalizing the signal according to said difference in level includes a pressure gauge emitting a signal which measures pressure at its level, a controllable correcting circuit equipped with a preselecting organ, a correcting circuit connected to and receiving said signal from said pressure gauge, said controllable correcting circuit and said organ being adapted to emit to said correcting circuit distinct signals which respectively correspond to distinct level differences between said pressure gauge and said intervention area, said distinct level differences being displayed by means of said preselecting organ.

15. Apparatus according to claim 1, wherein said correcting means for equalizing said measuring signal according to said difference in level includes a correcting circuit coupled with a controllable correcting circuit having a control organ, said correcting circuit being adapted by means of said controllable correcting circuit and said control organ to emit a correcting signal, said controllable correcting circuit permitting regulation of the amplitude of said correcting signals which corresponds to distinct level differences between said first means and said intervention area, said distinct level differences being displayed by means of said control organ.

16. Apparatus according to claim 1, wherein said second means includes a control circuit having a control organ and a comparator, said control circuit and said control organ being adapted to emit to a first input of said comparator distinct signals which correspond respectively to different values of said acceptable maximum pressure in said intervention area, said different values being selected by means of said control organ.

17. Apparatus according to claim 1, including at least one optical display device connected to said correcting means and adapted of visualizing the instant pressure in said intervention area.

18. Apparatus according to claim 1, including an optical display device connected to said correcting means for visualizing the instant pressure which is measured by said first means.

19. Apparatus according to claim 1, including an optical display device connected to said correcting means for visualizing the instant pressure in sad joining conduit.

* * * * *

UNITED STATES PATENT AND TRADEMARK OFFICE
CERTIFICATE OF CORRECTION

PATENT NO. : 4,795,424
DATED : January 3, 1989
INVENTOR(S) : Robert Burner

It is certified that error appears in the above-identified patent and that said Letters Patent is hereby corrected as shown below:

Title page:

Inventor's Address: 21 rue Damberg
F - 68200 Brunstatt
France

Signed and Sealed this
Nineteenth Day of December, 1989

*Attest:*

JEFFREY M. SAMUELS

*Attesting Officer*     *Acting Commissioner of Patents and Trademarks*